US00PP10160P

United States Patent [19]

Jacobsen

[11] Patent Number: Plant 10,160

[45] Date of Patent: Dec. 23, 1997

[54] POINSETTIA PLANT 'PEARL'

[75] Inventor: Peter Jacobsen, deceased, late of Skibby, Denmark, by Aase Jacobsen, executrix

[73] Assignee: Paul Ecke Ranch, Inc., Encinitas, Calif.

[21] Appl. No.: 630,433

[22] Filed: Apr. 10, 1996

[51] Int. Cl.[6] ..... A01H 5/00

[52] U.S. Cl. ..... Plt./86.2

[58] Field of Search ..... Plt./86.2

[56] References Cited

U.S. PATENT DOCUMENTS

| | | | |
|---|---|---|---|
| P.P. 4,000 | 12/1976 | Mikkelsen | Plt./86.2 |
| P.P. 4,221 | 3/1978 | Hrebeniuk | Plt./86.2 |
| P.P. 7,250 | 6/1990 | Gutbier | Plt./86.2 |

OTHER PUBLICATIONS

Poehlman, J.M. "Genetics in Relation to Plant Breeding" Breeding Field Crops 1959, Holt, Rinehart and Winston, Inc. New York, p. 43.

*Primary Examiner*—James R. Feyrer
*Attorney, Agent, or Firm*—Arnold, White & Durkee

[57] ABSTRACT

Poinsettia 'Pearl' is a new cultivar, distinguished by large white flower bracts, large leaves, strong thick stems and self-branching characteristics. 'Pearl' is a tetraploid sport of '21-85' (U.S. Plant Pat. No. 7,250) with the same flowering response and cultural requirements. The new plant produces a very desirable branched flowering pot plant. The new plant is resistant to epinasty after being confined to shipping containers. The post-production foliage and bract retention are good.

1 Drawing Sheet

BACKGROUND OF THE NEW PLANT

This new poinsettia cultivar originated as an induced tetraploid sport of Poinsettia Plant '21-85' (U.S. Plant Pat. No. 7,250) in my greenhouse in my greenhouse in Skibby, Denmark. It was induced through application of a 1% solution of colchicine to the cut surface of a vegetative poinsettia stem after the terminal apex was removed. Adventitious shoots that arose from the treated area were removed and placed in a propagation environment to produce roots. From among these new plants the subject plant 'Pearl' was selected. It was selected because of its strong stems, self branching, large creamy white flower bracts and large green leaves, traits that help distinguish it from other poinsettia cultivars, and seem to make it a desirable plant for commercial greenhouse production. After selection, 'Pearl' was vegetatively reproduced from stem cuttings for test purposes in Encinitas, Calif. By subjecting clones of this plant to successive generations of vegetative propagation, it was demonstrated that the distinctive characteristics of 'Pearl' held true from generation to generation. 'Pearl' differed from its parent '21-85' in having larger flower bracts, larger leaves, longer leaf petioles, thicker stems and larger cyathia.

DESCRIPTION OF THE PHOTOGRAPHS

Poinsettia 'Pearl' is illustrated in the accompanying color photographs.

The upper photo is a side view of one branched 'Pearl' plant per pot in full flower. The lower photo is a top view of the subject plant 'Pearl', left, and the parent plant '21-85', right, showing flower and bract formation.

DESCRIPTION OF THE PLANT

The following is a detailed description of this new poinsettia as observed in Encinitas, Calif., USA during December 1994. Observations were recorded from flowering plants, grown as one branched plant per pot. The pot was 14 cm in diameter and 11 cm in height. Color designations are compared to the 1986 edition of R.H.S. Colour Chart, first published in 1966 by The Royal Horticultural Society, London, England.

THE PLANT

The following chart summarizes some of the differences between 'Pearl' and poinsettia '21-85' (U.S. Plant Pat. No. 7,250).

| Plant | 'Pearl' | '21-85' |
|---|---|---|
| Chromosomes | 56 | |
| Plant Width | 58 cm | 53 cm |
| Bract diameter | 35 cm | 30 cm |
| Main stem diam | 10 mm | 8 mm |
| Axillary stem diam | 8 mm | 6 mm |
| Leaf dimensions | 13 × 9 cm | 11 × 8 cm |
| Bract dimensions | 15 × 10 cm | 14 × 8 cm |
| Cyathium dimensions | 9 × 8 mm | 6 × 7 mm |
| Internode length | 0.9 cm | 1.2 cm |
| leaf color | RHS147A | RHS137A |
| bract color | RHS158C-D | RHS155A-1D |

While the differences in sizes of plant parts listed in the above chart might be expected between the tetraploid 'Pearl' and the diploid mother plant '21-85', there are several other characteristics of 'Pearl' which were not predictable. 'Pearl' has a more compact growth habit than '21-85', resulting in fewer chemical growth retardant applications for height control in commercial production. The internode length of 'Pearl' was about 0.9 cm compared to 1.2 cm for '21-85' grown under the same environmental and cultural conditions. The foliage color is darker green for 'Pearl', darker than R.H.S.147A compared to R.H.S.137A for '21-85'. The flower bracts of 'Pearl' are more erect and held in a more horizontal plane. Mature bracts of '21-85' tend to droop slightly. The bract color of 'Pearl' is a creamy white, R.H.S.158C-D, compared to the bone white, R.H.S.155A-1D of '21-85'.

Origin: Induced tetraploid sport of '21-85' (U.S. Plant Pat. No. 7,250), induced by application of a 1% solution of colchicine to a vegetative poinsettia stem.

Classification:

*Botanical.*—*Euphorbia pulcherrima* Willd.

*Common name.*—Poinsettia.

*Cultivar name.*—'Pearl'.

Form: Shrub.

Height: Medium.

Growth habit: As a single stemmed plant, upright and vigorous with self-branching side shoots. The application of a chemical growth retardant may be needed to restrict height for commercial pot plant production. I observed one branched plant per pot with an overall height of 40 cm and an overall width of 58 cm. The bract diameter of indiivdual flowers was 35 cm.

Branching: Axillary branches will develop and terminate in a flower without pinching. However, it is usually desirable to pinch 'Pearl' before flower induction and remove all teminal dominance. Then, all axillary branches will develop uniformly and at a faster rate.

Growth rate: Rooting of stem cutting occurs in 12–18 days under intermitten mist.

Flowering: The plant will flower in eight to nine weeks under continuous long night conditions and night temperatures of 16°–18° C. Like its parent, '21-85', 'Pearl' will be in full bloom in late November in the northern hemisphere under natural daylength conditions.

Foliage: At flowering, plants were observed with dark green leaves, one leaf per node. The leaves were of large size, leaf blades typically being 13 cm long and 9 cm wide with leaf petioles 6–7 cm long. The upper leaf surface was glabrous and the under surface was pubescent.

*Leaf shape.*—Typical leaves are generally ovate with obtuse bases and acuminate tips. Leaf margins are mostly entire with an occasional lobe on one side of the lower-most leaves.

*Color.*—Upper side — Green, slightly darker than R.H.S. 147A. Under side — Green, a little darker than R.H.S. 147B.

Bracts: Generally there were 12–14 creamy white bracts of various sizes subtending the cyathia. The primary bracts were large, have blades typically 15 cm long and 10 cm wide with petioles 4–5 cm long.

*Shape.*—Primary bracts were ovate with acute to obtuse bases and acuminate tips. Margins were entire or weakly lobed with one small indentation on either side of the bract. Secondary bracts were ovate to elliptic and had entire margins.

*Color.*—Upper side — Creamy white. R.H.S. 158 C-D. Under side — Creamy white. R.H.S. 158 C-D.

Flowers: Generally, 10–12 large cyathia (flowers) were present when the plant was in full bloom. Each cyathium was about 8 mm long and 9 mm wide, green in color, and fringed with yellow at the distal end. Sometimes one, but usually two yellow nectar cups protrude form the side of each cyathium. The flower pedicel was also green and about 6 mm in length. The stamens protruding from the cyathia were white. The anthers were bifurcate with copious yellow pollen. The stigmas were greenish and trifurcate. Cyathia retention was about three weeks beyond the time the flower was fully mature.

*Nectar exudate.*—Present, abundant.

*Seed formation.*—Self-incompatible.

*Fertility.*—Not observed.

Post production: 'Pearl' was resistant to epinasty after being confined to shipping containers. The foliage and bract retention were good.

What is claimed is:

1. A new and distinct Poinsettia plant, substantially as herein shown and described, distinguished by its strong thick stems, large white bracts, self branching, large leaves and good leaf and bract retention in the consumer environment.

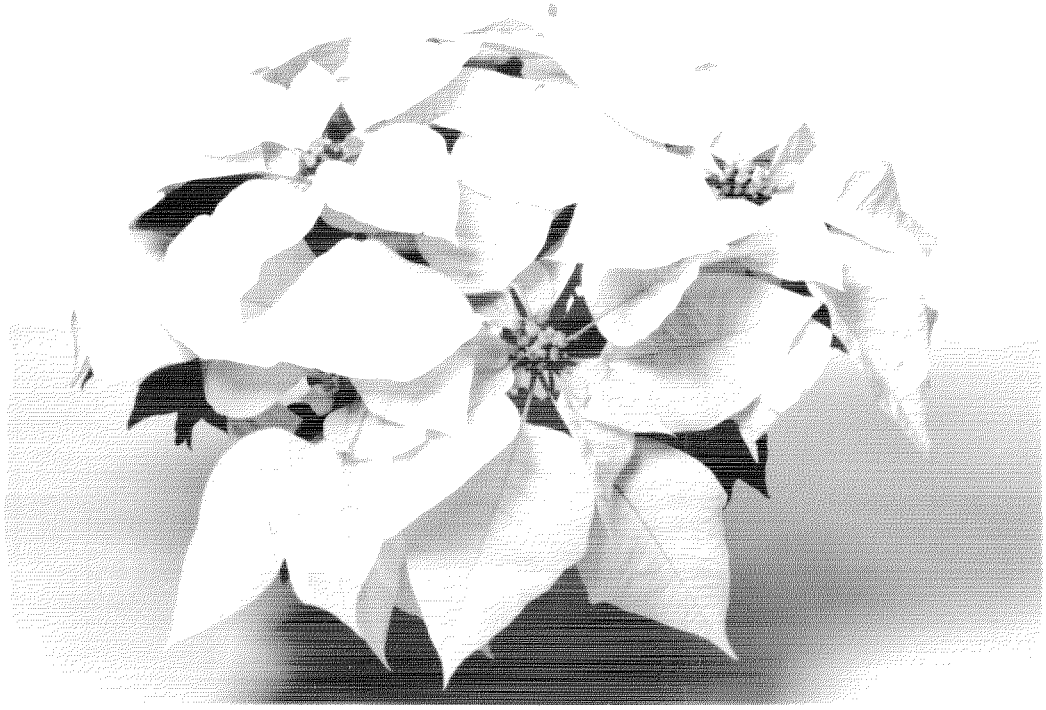
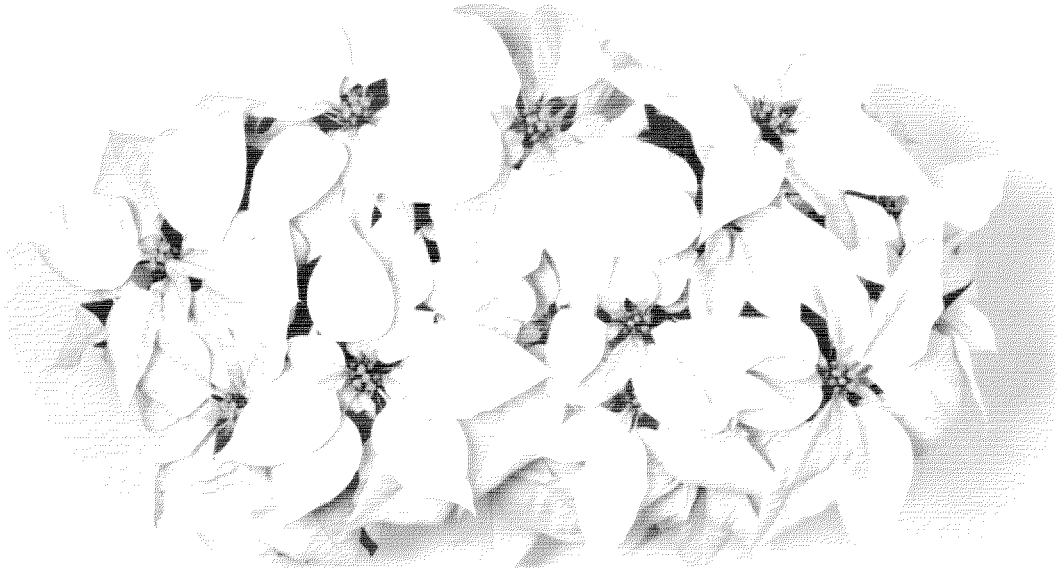

* * * * *